United States Patent
Bonnin et al.

(10) Patent No.: US 8,672,478 B2
(45) Date of Patent: Mar. 18, 2014

(54) OPHTHALMIC LENS ARRANGEMENT AND AN APPARATUS FOR DEMONSTRATING A PLURALITY OF OPTICAL FUNCTIONS AND A METHOD FOR DEMONSTRATING A PLURALITY OF OPTICAL FUNCTIONS

(75) Inventors: Thierry Bonnin, Charenton le Pont (FR); Benjamin Rousseau, Charenton le Pont (FR)

(73) Assignee: Essilor International (Compagnie Generale d'Optique), Charenton le Pont (FR)

( * ) Notice: Subject to any disclaimer, the term of this patent is extended or adjusted under 35 U.S.C. 154(b) by 0 days.

(21) Appl. No.: 13/514,903

(22) PCT Filed: Dec. 10, 2010

(86) PCT No.: PCT/EP2010/069346
§ 371 (c)(1),
(2), (4) Date: Jun. 8, 2012

(87) PCT Pub. No.: WO2011/070139
PCT Pub. Date: Jun. 16, 2011

(65) Prior Publication Data
US 2012/0274892 A1 Nov. 1, 2012

(30) Foreign Application Priority Data

Dec. 10, 2009 (EP) .................................. 09306208

(51) Int. Cl.
*G02C 7/12* (2006.01)
(52) U.S. Cl.
USPC .............. 351/159.56; 351/159.4; 351/159.42; 351/159.48; 351/159.7
(58) Field of Classification Search
CPC ............ G02C 7/02; G02C 7/022; G02C 7/04; G02C 7/041; G02C 7/06; G02C 7/061; G02C 7/12
USPC ............ 351/159.01, 159.02, 159.03, 159.06, 351/159.16, 159.39, 159.4, 159.42, 159.48, 351/159.56, 159.7, 159.73, 159.81
See application file for complete search history.

(56) References Cited

U.S. PATENT DOCUMENTS

| 5,712,721 A | 1/1998 | Large |
| 2004/0156021 A1 | 8/2004 | Blum et al. |

(Continued)

FOREIGN PATENT DOCUMENTS

| EP | 0308705 A2 | 3/1989 |
| GB | 1252276 | 11/1971 |

(Continued)

OTHER PUBLICATIONS

Katz et al., "Highly Birefringent Materials Designed Using Coordination Polymer Synthetic Methodology," Angew. Chem. Int. Ed. 46:8804-8807, 2007.

(Continued)

*Primary Examiner* — Darryl J Collins
(74) *Attorney, Agent, or Firm* — Seed IP Law Group PLLC

(57) ABSTRACT

The invention relates to an ophthalmic lens arrangement (10) comprising a polarizer (11) for polarizing light in a polarization axis; at least one lens cell (13) including a switchable light rotator; a lens member (15) having birefringence properties such that incident light encounters a first refractive index n on an ordinary axis or a second refractive index on an extraordinary axis according to the rotation of the incident light; and a sub lens member (17) having a refractive index n; characterized in that: the or each rotator is operable to rotate incident light by 0° or by 90°, and the polarizer is arranged such that the polarization axis coincides with either the ordinary axis or the extraordinary axis of the or each lens member. The invention further relates to an apparatus for and a method for demonstrating a plurality of optical functions.

18 Claims, 12 Drawing Sheets

(56) References Cited

U.S. PATENT DOCUMENTS

| | | |
|---|---|---|
| 2012/0050681 A1 | 3/2012 | Bonnin et al. |
| 2012/0050682 A1 | 3/2012 | Bonnin et al. |

FOREIGN PATENT DOCUMENTS

| | | |
|---|---|---|
| JP | 63135916 A | 6/1988 |
| JP | 11352445 A | 12/1999 |
| JP | 2002323680 A | 11/2002 |

OTHER PUBLICATIONS

Kern, S.P., "Bifocal, electrically switched intraocular and eyeglass molecular lenses," Ophthalmic Optics SPIE 601:155-158, Dec. 1, 1985.

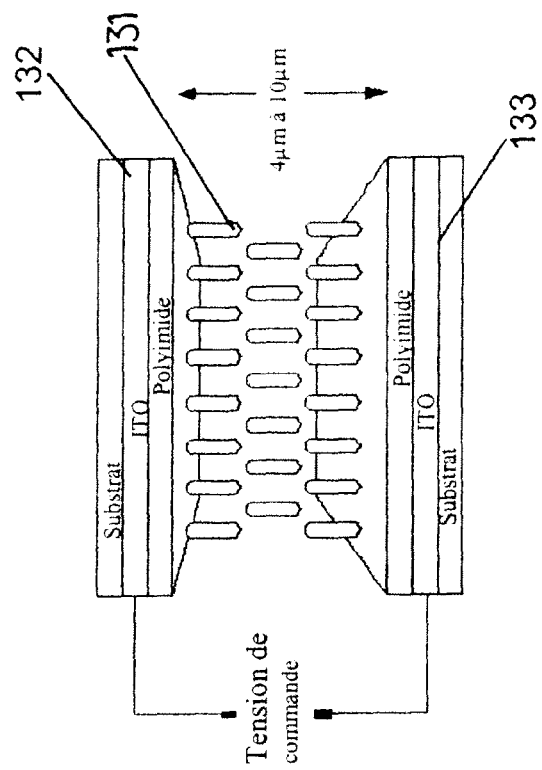
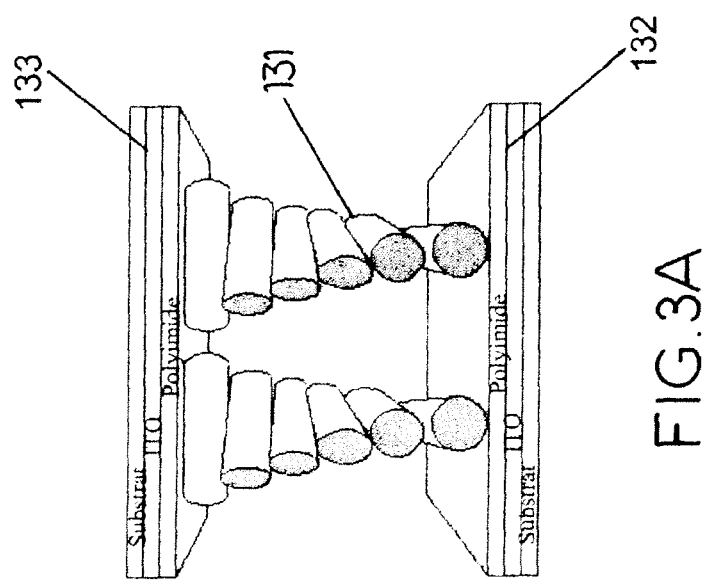

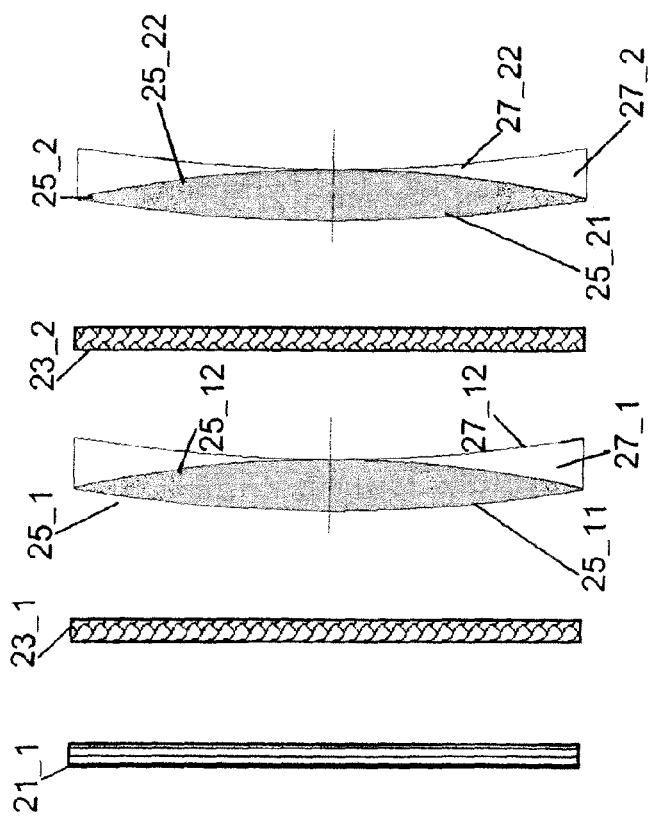
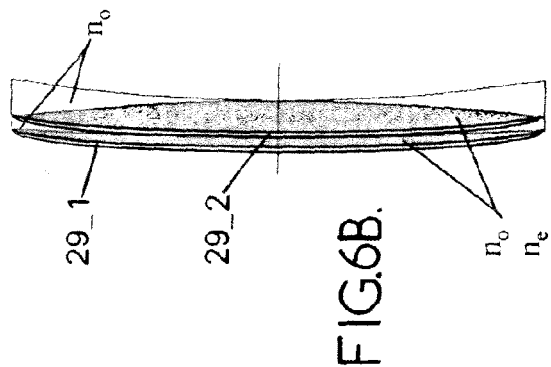

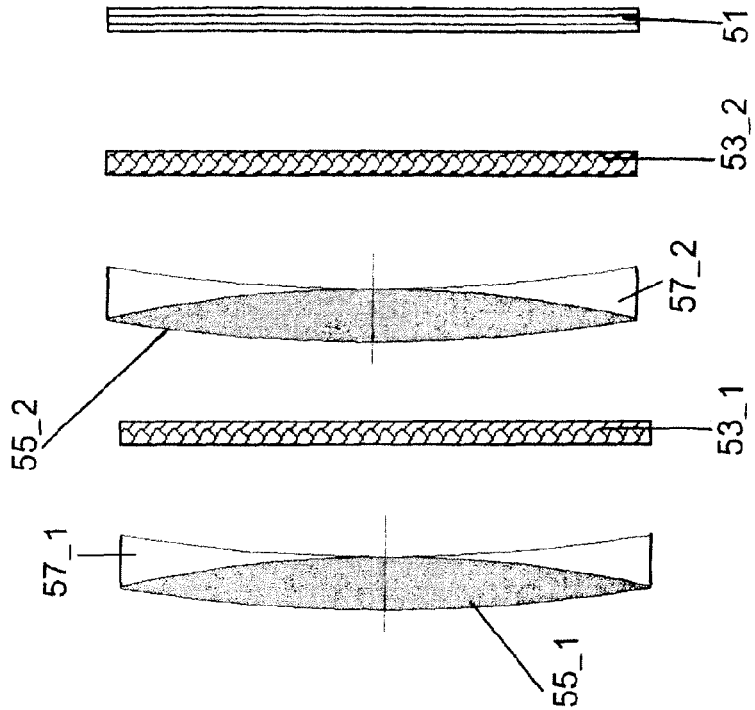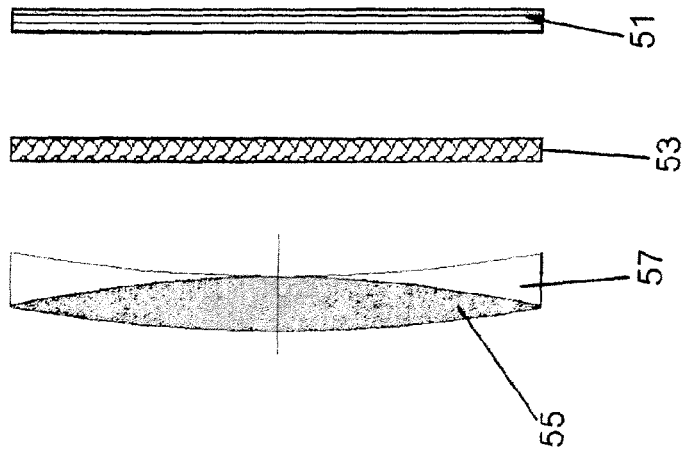

OPHTHALMIC LENS ARRANGEMENT AND AN APPARATUS FOR DEMONSTRATING A PLURALITY OF OPTICAL FUNCTIONS AND A METHOD FOR DEMONSTRATING A PLURALITY OF OPTICAL FUNCTIONS

FIELD OF THE INVENTION

The present invention relates in general to an ophthalmic lens arrangement for compensating for visual defects. In particular the invention relates to an ophthalmic lens arrangement having a lens member having birefringence properties. The invention further relates to an apparatus and a method for demonstrating a plurality of optical functions.

BACKGROUND OF THE INVENTION

Ophthalmic lens for the compensation of eyesight defects are well known. One of the main problems encountered in the field of ophthalmic correction is the correction of the condition presbyopia where the eye exhibits a progressively diminished ability with age to focus on near objects. Typically the condition is addressed by the use of bifocal or multifocal contact lenses that attempt to correct both near and far vision with the same lenses, the lens having a far vision region and a near vision region. Progressive ophthalmic lenses usually comprise a far vision region, a near vision region, and a progressive corridor (or channel) there between. The progressive corridor provides a gradual power progression from the far vision zone to the near vision zone without a dividing line or a prismatic jump.

While the use of such lenses can help to provide a net vision at a range of distances they can also lead to artifacts, such as distortion, spatial restrictions problems of adaptation which complicate the design, manufacture and the use of such lenses. Unifocal lenses on the other hand do not lead to such defects by only enable one range of good quality vision to be provided.

Traditionally prescribing ophthalmic lens to a wearer involves fitting a potential wearer having an eyesight defect with ophthalmic lenses having different optical characteristics and then selecting the lenses which provide the best optical performance for the wearer. Such techniques suffer the drawback that the wearer has to go through the process of putting off and taking off a number of spectacles and may only be exposed to a limited selection of lenses which may not include the optical lens optimal for correcting the particular eyesight defect.

US 2004/0156021 discloses an ophthalmic lens arrangement according to the prior art. Such prior art arrangement suffers a number of drawbacks such as the limitation in of the size of the optical lens, the limitation in the amplitude of optical power variation, the limitation in the chromatic aberration and the arising of high order diffraction modes.

SUMMARY OF THE INVENTION

The present invention has been devised with the foregoing drawbacks in mind.

Accordingly, a first aspect of the invention provides an ophthalmic lens arrangement comprising:
a polariser for polarising light in a polarisation axis;
at least one lens cell including
a switchable light rotator;
a lens member having birefringence properties such that incident light encounters a first refractive index $n_o$ on an ordinary axis or a second refractive index $n_e$ on an extraordinary axis according to the rotation of the incident light; and
a sub lens member having a refractive index n;
wherein,
the or each rotator is operable to rotate incident light by 0° or by 90°,
the polariser is arranged such that the polarisation axis coincides with either the ordinary axis or the extraordinary axis of the or each lens member, and
the intermediary surface between the lens member and the sub-lens member of the at least one lens cell is a progressive surface.

The invention may also concern an ophthalmic lens arrangement comprising: a polariser for polarising light in a polarisation axis;
at least one lens cell including a switchable light rotator; a lens member having birefringence properties such that incident light encounters a first refractive index $n_o$ on an ordinary axis or a second refractive index $n_e$ on an extraordinary axis according to the rotation of the incident light; and a sub lens member having a refractive index n; characterized in that: the or each rotator is operable to rotate incident light by 0° or by 90°, and the polariser is arranged such that the polarisation axis coincides with either the ordinary axis or the extraordinary axis of the or each lens member.

In embodiments of the invention:
the refractive index of at least one sub lens member may be $n_o$ or $n_e$.
the external faces of the at least one lens cell may be matched such that the optical power of the respective lens cell is zero along the ordinary axis or along the extraordinary axis.
at least one rotator is adjusted to rotate the incident light to provide an optical power of the ophthalmic lens arrangement within a predetermined optical power range ΔP the predetermined optical power range ΔP depending on the refractive index n of the or each sub lens member.
an external face of the ophthalmic lens arrangement may be machinable to conform to an optical lens prescription.
the intermediary surface between the lens member and the sub-lens member of at least one lens cell may be a complex surface providing an optical function.
the intermediary surface between the lens member and the sub-lens member of at least one lens cell may be a sphero-toric surface.
at least one rotator may be switchable from a first state to a second state providing a change in the dioptric values of the ophthalmic lens arrangement. The dioptric values may comprise, for example, the spherical power, the astigmatic power, the prismatic power or a combination thereof.
the or each rotator may be switched according to the proximity of an object being viewed through the ophthalmic lens arrangement.
A second aspect of the invention provides apparatus for demonstrating a plurality of optical functions, the apparatus comprising: an ophthalmic lens arrangement as described above, and having a plurality of lens cells in which the dioptric surface between the lens member and the sub-lens members is a complex surface; and a selector for switching the rotator of one or more of the lens cells according to the optical function to be demonstrated.

In embodiments of the invention:
the refractive index of at least one sub lens member may be $n_o$ or $n_e$ and the external faces of the corresponding lens cells may be matched;
the selector may be arranged to select the optical function to be demonstrated by switching the rotator of the said at least one sub lens member such that the optical power of the respective lens cell is zero along the ordinary axis or along the extraordinary axis is zero, and by switching the rotator of at least one other lens cell so that the at least one other lens cell has a non-zero optical power.
the selector may be operable to switch the rotator of each lens cell such that a single lens cell demonstrating the optical function to be demonstrated is sequentially selected to have a non zero optical power while the remaining lens cells have a zero optical power.
the optical function to be demonstrated may be selected from the group including at least progressive design, and astigmatism design.

A third aspect of the invention provides a method of demonstrating a plurality of optical functions of an ophthalmic lens, the method comprising: selecting an optical function to be demonstrated; polarizing light; transmitting light through a plurality lens cells wherein each lens cells includes a lens member having birefringence properties such that incident light encounters a first refractive index $n_o$ or a second refractive index $n_e$ according to the rotation of the incident light; and a sub lens member having a refractive index n; rotating the light entering each lens member from a first incident direction by 0° or by 90° according to the optical function to be demonstrated.

It will be appreciated that the light may be polarised before or after being transmitted through a lens cell.

In embodiments of the invention the method may further include switching the rotator of each lens cell such that a single lens cell demonstrating the optical function to be demonstrated is sequentially selected to have a non zero optical power while the remaining lens cells have a zero optical power.

At least part of the methods according to the invention may be computer implemented. The methods may be implemented in software on a programmable apparatus. They may also be implemented solely in hardware or in software, or in a combination thereof.

Since the present invention can be implemented in software, the present invention can be embodied as computer readable code for provision to a programmable apparatus on any suitable carrier medium. A tangible carrier medium may comprise a storage medium such as a floppy disk, a CD-ROM, a hard disk drive, a magnetic tape device or a solid state memory device and the like. A transient carrier medium may include a signal such as an electrical signal, an electronic signal, an optical signal, an acoustic signal, a magnetic signal or an electromagnetic signal, e.g. a microwave or RF signal.

BRIEF DESCRIPTION OF THE DRAWINGS

Embodiments of the invention will now be described, by way of example only, and with reference to the following drawings in which:—

FIG. 3A is a schematic diagram illustrating an example of a polarity rotator in an off state for any one of the embodiments of the invention;

FIG. 3B is a schematic diagram illustrating an example of the polarity rotator in an on state for any one of the embodiments of the invention;

FIGS. 6A and 6B are schematic diagrams of an ophthalmic lens arrangement according to a second embodiment of the invention;

FIGS. 10A and 10B are schematic diagrams of an ophthalmic lens arrangement according to a fifth embodiment of the invention;

DETAILED DESCRIPTION

A first embodiment of a method of, of the invention will be described with reference to FIGS. 1A &B and 2.

Figure 1B:
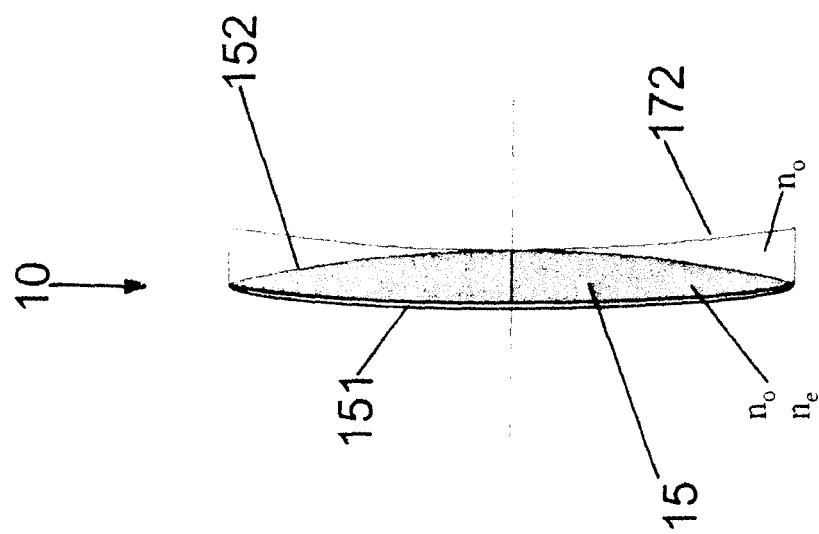
FIGS. 1A and 1B are schematic diagrams of an ophthalmic lens arrangement according to a first embodiment of the invention.
Figure 1A:
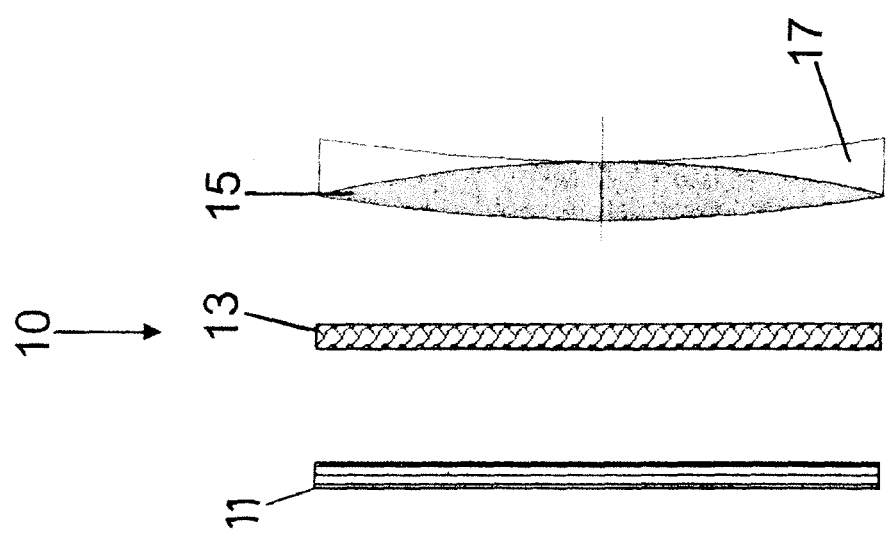

FIG. 1A is a schematic diagram of an ophthalmic lens arrangement 10 according to the first embodiment of the invention including a polariser 11, a switchable rotator 13, a lens 15 and a sub lens 17. The polariser 11 is a linear polariser which can polarise light in a polarisation axis defining the direction of the electric field of the light wave. The lens 15 has birefringence properties such that light passing through the lens medium follows different optical paths through the lens medium depending on its polarization. The light thus according to its direction of polarization either encounters either an ordinary refractive index $n_o$ on an ordinary axis or an extraordinary refractive index $n_e$ on an extraordinary axis. To this end the lens 15 is made of $CaCO_3$ material. It will be understood that in alternative embodiments, the lens made be made of any suitable birefringent polymer material. The external faces 151 and 152 of the lens 15 are provided with curvature each defined by a radius R in order to form a lens. Because of the birefringence properties the lens 15 has two foci, a first focal $f_o$ corresponding to the ordinary refractive index $n_o$ and a second focal $f_e$ corresponding to the extraordinary refractive index $n_e$. In this embodiment of the invention the sub lens 17 has a fixed refractive index $n_o$ corresponding to the ordinary refractive index $n_o$ of the lens 15.

Figure 2:
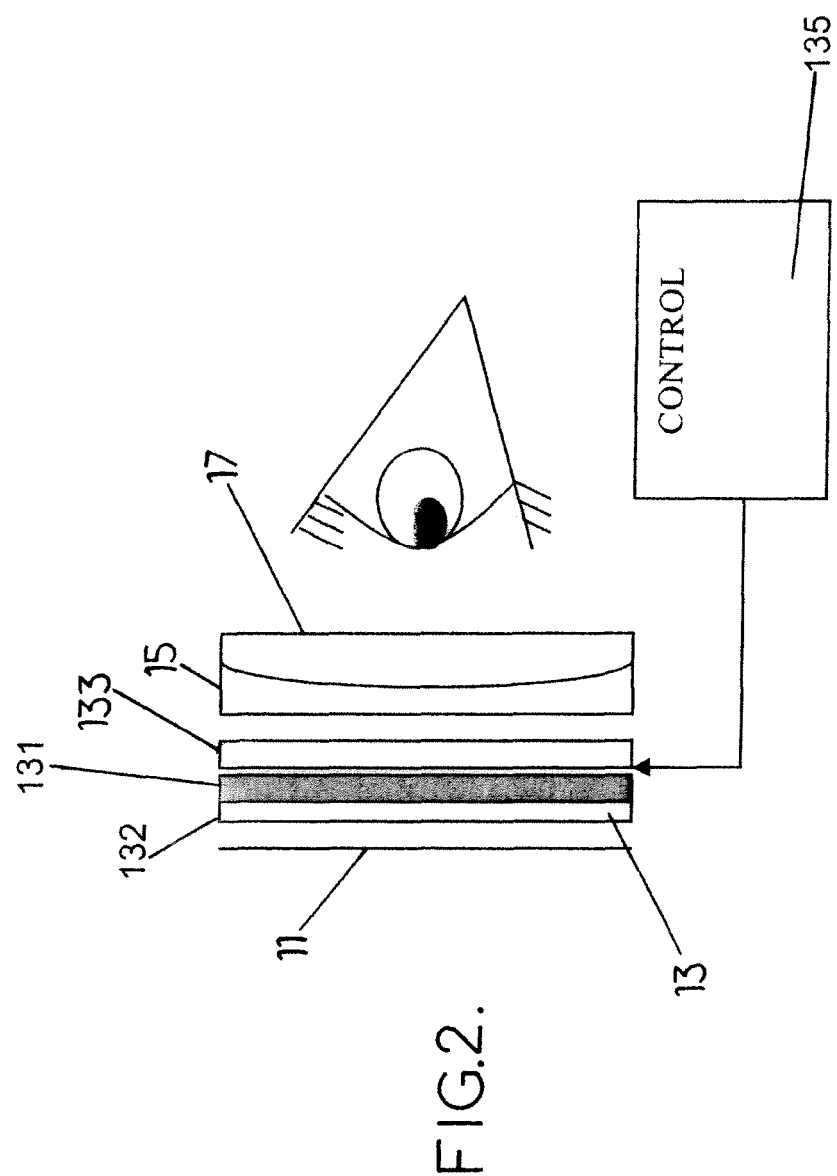
FIG. 2 is a schematic diagram of an ophthalmic lens arrangement according to the first second embodiment of the invention.

Referring to FIG. 2 light entering the ophthalmic arrangement 10 is linearly polarized in a polarization axis by the polarizer 11. According to a received control signal from control 135 switchable rotator 13 can change the direction of polarization by 0° or 90° of the light from the original polarization axis.

With reference to FIG. 3A the rotator 13 comprises a liquid crystal structure layer 131 placed between two substrate configurations 132 and 133 each substrate configurations including an outer substrate layer, an ITO (indium tin oxide) layer and an inner polyamide layer. The operation of the rotator 13 is based on the properties of liquid crystals. In a resting state, liquid crystals tend to organize themselves in a helical structure. Polarised light naturally follows a path along this helical structure. A liquid crystal layer can be configured to only allow a 90° rotation of this helical structure so that the polarization of light passing through the structure can be rotated through an angle of 90° with respect to the original polarization direction. If an electric field is then applied across the liquid crystal layer via substrates 132 and 133 acting as electrodes, the liquid crystal molecules which are also electric dipoles will orientate themselves parallel to the electric field as illustrated in FIG. 3B. In this orientation the light follows a path along the orientation of the molecules and undergoes no rotation of polarization. The control voltage generating the electric field is to the order of 10V and the absorbed power is also very low. The thickness of the rotator 13 and the liquid crystal layer 131 in this embodiment is less than 10 µm. It will be appreciated that in some embodiments of the invention the lens themselves may act as substrates.

Figure 4B:
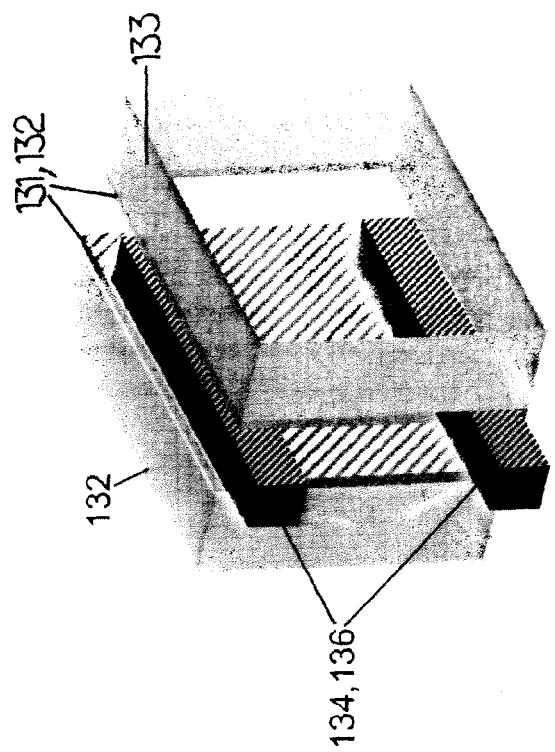
FIG. 4B is a view in perspective of connection of a polarity rotator for any one of the embodiments of the invention.
Figure 4A:
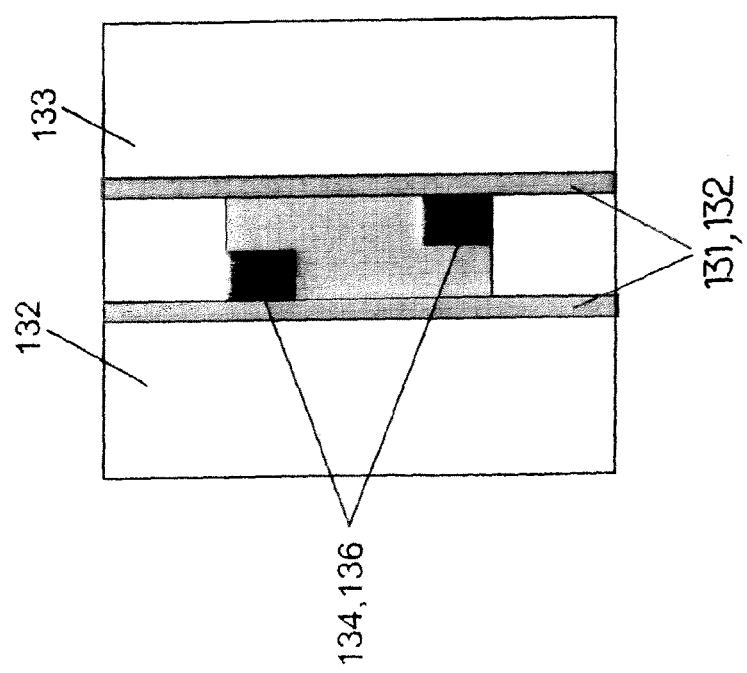
FIG. 4A is a schematic diagram illustrating an example of connection of a polarity rotator for any one of the embodiments of the invention.

Two connectors 134 and 135 are provided for each substrate 132 and 133. if the optical lens arrangement has to be machined or cut as part of the manufacturing process for an optical lens product the connections to the electrodes 132 and 133 are made after the manufacturing steps. Empty cells as illustrated in FIGS. 4A and 4B may be used to make the connection so that the connectors are not cut during manufacture of the ophthalmic lens arrangement when it is used as an ophthalmic lens product to be used as a lens in spectacles for example.

Figure 5A:
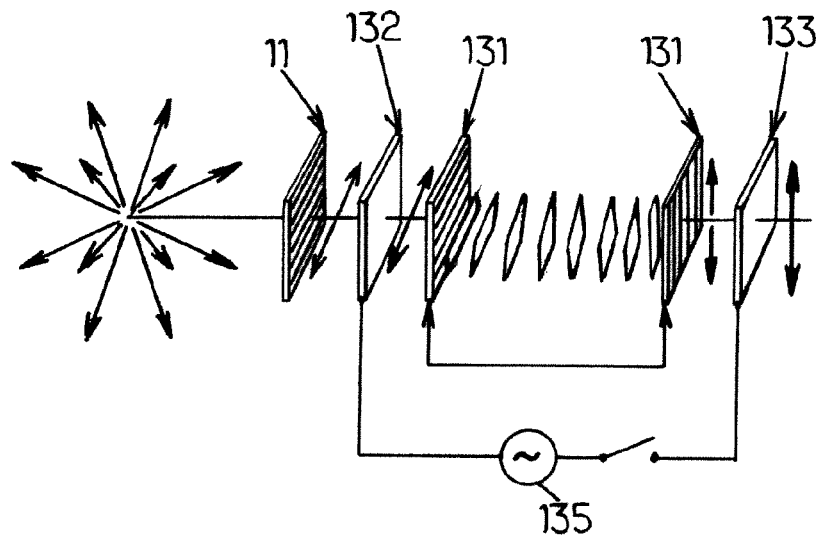
FIG. 5A is a schematic diagram illustrating the operation of the polarity rotator of FIG. 3A in an off state for any one of the embodiments of the invention.
Figure 5B:
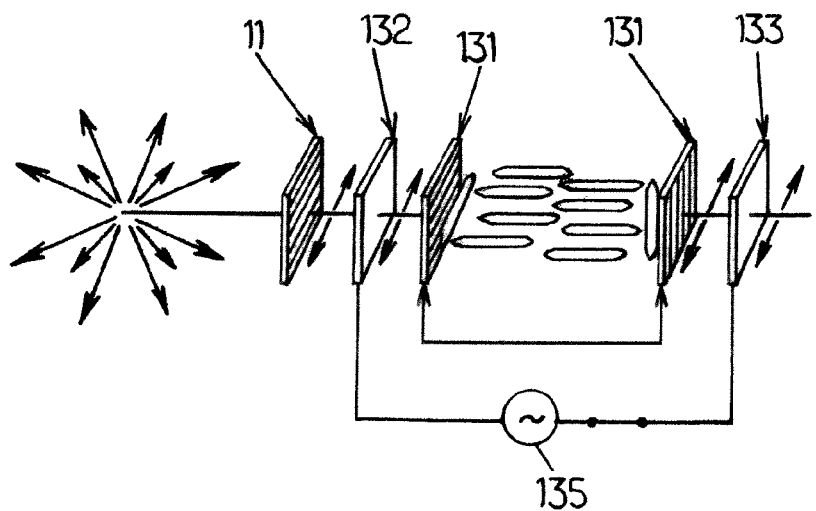
FIG. 5B is a schematic diagram illustrating the operation of the polarity rotator of FIG. 3B in an on state for any one of the embodiments of the invention.

FIGS. 5A and 5B illustrate the operation of the rotator 13 and the polarizer 11. In FIG. 5A the liquid crystals of the liquid crystal layer 131 are in the resting state since no voltage is applied between substrates 132 and 133. Light is firstly polarized by the linear polarizer 11 along a horizontal polarization axis. The polarized light then enters the rotator 13 and follows the structure of liquid crystals arranged in a natural helical alignment generally parallel to the substrates 132 and 133. The polarization of the light undergoes a rotation of 90° with respect to the original horizontal direction and is polarized in a vertical direction.

In FIG. 5B an electric field is applied across liquid crystal layer 131 between substrates 132 and 133 to align the liquid crystals along the direction of the electric field. AC current is used so that the liquid crystal is not electrically polarized. In this configuration the light follows the alignment of the crystals and the polarization of the light with respect to the direction of polarization of light on entering the rotator remains unchanged.

The rotation or non rotation of the polarization of the light enables the first focal $f_o$ corresponding to the ordinary refractive index $n_o$ or the second focal $f_e$ corresponding to the extraordinary refractive index $n_e$ of lens 15 to be selected.

Sub lens 17 has a refractive index $n_o$. The curvature of the external faces of the ophthalmic combination lens 15 and sub lens 17 are matched i.e. the curvature of surface 151 of lens 15 and surface 172 of sub lens 17 are matched.

In operation when the rotator 13 is in the resting state the light encounters the ordinary refractive index $n_o$ of lens 15 and the refractive index $n_o$ of sub lens 17. A combined lens of uniform refractive index $n_o$ with parallel matched faces and thus of zero power is provided. However, on activation of the rotator 13 the extraordinary refractive index $n_e$ of lens 15 is selected. In this situation the light encounters the extraordinary refractive index $n_e$ in the lens 15 and is refracted at the interface of the lens 15 and the sub lens 17 at surface 152 of lens 15 since the refractive index of the sub lens is $n_o$. In this case an optical effect relative to the curvature of the interface and related to the differential $n_e - n_o$ is created. A lens of power $P_e$ is thus provided:

$$P_e = \Delta n \left( \frac{1}{R_1} - \frac{1}{R_2} \right) \quad (1)$$

where $\Delta n$ represents the difference between the ordinary refractive index $n_o$ of the lens 15 and the extraordinary refractive index $n_e$ of the lens 15; $R_1$ represents the curvature radius of front face 151 of the combined lens; and $R_2$ represents the curvature radius of the interface surface 152 between the lens 15 and the sub-lens 17.

As way of illustrating example only, if lens 15 is made of $CaCO_3$ material, $\Delta n=0.17$, $R_1=200$ mm and $R_1=147$ mm a switchable ophthalmic lens arrangement is provided where the power of the combined lens is switchable from plan power to a power of 2 dioptres thereby providing bifocal lens switchable between a far vision state with a full field of view and a near vision state with a full field of view.

The combination of a rotator 13, a lens 15 and a sub lens 17 can be seen as a lens cell 19. Further embodiments of the invention may include multiples of such lens cells.

For example with reference to FIG. 6A and FIG. 6B an ophthalmic lens arrangement according to a second embodiment of the invention includes a polariser 21, a first lens cell 29_1 made up of a first rotator 23_1, a first lens 25_1 and a first sub-lens 27_1, and a second lens cell 29_2 made up of a second rotator 23_1, a second lens 25_2 and a second sub-lens 27_2. The lens cells 29_1 and 29_2 are each identical to the lens cell of the first embodiment.

Each lens cell 29_1 or 29_2 can be controlled independently by switching the rotator 23_1 or 23_2 of the corresponding lens cell. Consequently depending on the switching of the rotators 23_1 and 23_2 a set of different optical powers may be provided In the case where the two rotators 23_1 and 23_2 are activated such that polarised light encounters the extraordinary refractive index $n_e$ of both the lens 25_1 and the lens 25_2 the optical power $P_T$ of the ophthalmic lens arrangement can be based on a lens-maker equation for a lens of negligible thickness, and is given by:

$$P_T = \Delta n \left( \frac{2}{R_1} - \frac{1}{R_2} - \frac{1}{R_3} \right) \quad (2)$$

where $\Delta n$ represents the difference between the ordinary refractive index $n_o$ of the lens 25_1 and 25_2 and the extraordinary refractive index $n_e$ of the lens 25_1 and 25_2; $R_1$ represents the curvature radius of front face 25_11 of lens 25_1; and $R_2$ represents the curvature radius of the interface surface 25_12 between the lens 25_1 and the sub-lens 27_1, and $R_3$ represents the curvature radius of the interface surface 25_22 between the lens 25_2 and the sub-lens 27_2.

In the case where the first rotator 23_1 is activated such that polarised light encounters the extraordinary refractive index $n_e$ of the lens 25_1, while the second rotator 23_2 is inactive such that polarised light encounters the ordinary refractive index $n_o$ of the lens 25_2, the optical power $P_1$ of the ophthalmic lens arrangement is given by:

$$P_1 = \Delta n \left( \frac{1}{R_1} - \frac{1}{R_2} \right) \quad (3)$$

In the case where the first rotator 23_1 is inactive such that polarised light encounters the ordinary refractive index $n_o$ of the lens 25_1, while the second rotator 23_2 is activated such that polarised light encounters the extraordinary refractive index $n_e$ of the lens 25_2, the optical power $P_2$ of the ophthalmic lens arrangement is given by:

$$P_2 = \Delta n \left( \frac{1}{R_1} - \frac{1}{R_3} \right) \quad (4)$$

In the case where the two rotators 23_1 and 23_2 are inactive such that polarised light encounters the ordinary refractive index $n_0$ of both the lens 25_1 and the lens 25_2 the optical power $P_3$ of the ophthalmic lens arrangement is given by:

$$P_3 = 0 \quad (5)$$

As way of example, again using $CaCO_3$ material for lens 25_1 and 25_2 and with the following parameters:

| Δn | R1 | R2 | R3 |
|---|---|---|---|
| 0.17 | 200 mm | 1700 mm | −425 mm |

A four focal full field of view lens arrangement is provided in which the focal can be switched between the following:

| C2 | C1 | P(Dpt) | Focal(m) |
|---|---|---|---|
| 0 | 0 | 0 | ∞ |
| 0 | 1 | 2 | 0.5 |
| 1 | 0 | 1.25 | 0.8 |
| 1 | 1 | 0.75 | 1.33 |

Where C2 and C1 correspond to the inactive (0) or activated state (1) of the rotators 23_1 and 23_2 respectively.

Figure 7B:
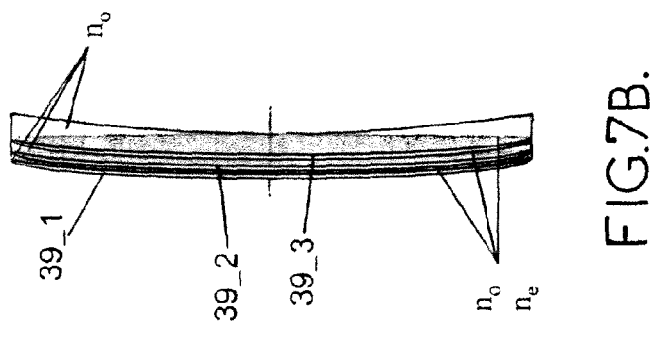
FIGS. 7A and 7B are schematic diagrams of an ophthalmic lens arrangement according to a third embodiment of the invention.
Figure 7A:
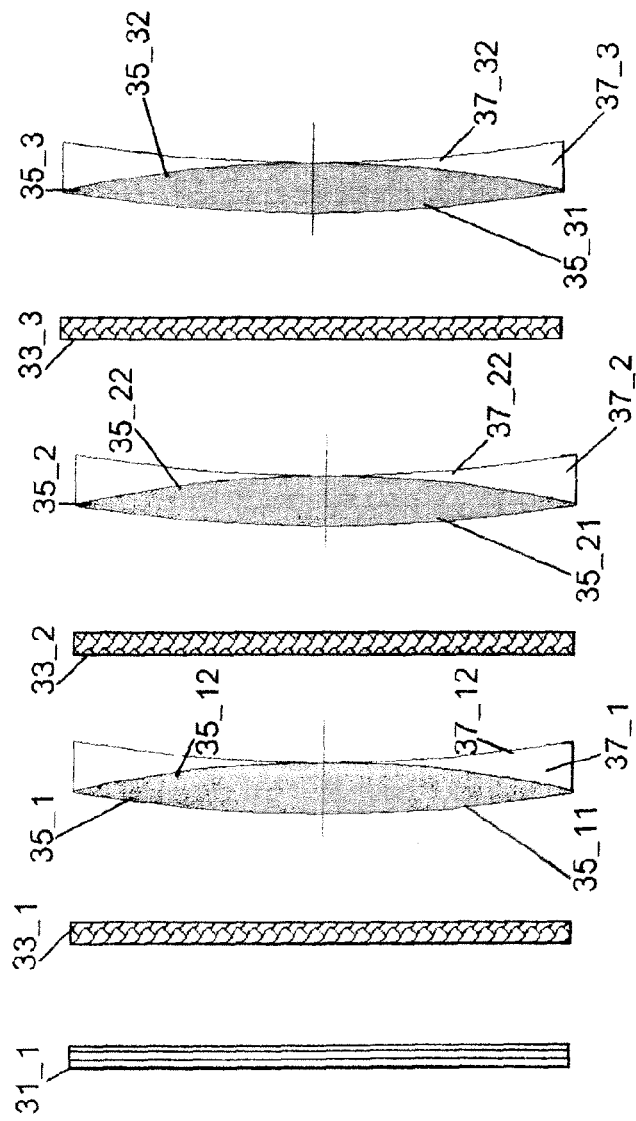

With reference to FIGS. 7A and 7B an ophthalmic lens arrangement according to a third embodiment of the invention includes a polariser 31, a first lens cell 39_1 made up of a first rotator 33_1, a first lens 35_1 and a first sub-lens 37_1, a second lens cell 39_2 made up of a second rotator 33_1, a second lens 35_2 and a second sub-lens 37_2, and a third lens cell 39_3 made up of a third rotator 33_3, a third lens 35_3 and a third sub-lens 37_3. The lens cells 39_1, 39_2 and 39_3 are each identical to the lens cell of the first embodiment. The power $P_T$ of the resulting ophthalmic arrangement when each of the rotators 33_1, 33_2 and 33_3 are activated so that the extraordinary refractive index $n_e$ is encountered in each lens 35 is given by:

$$P_T = \Delta n \left( \frac{3}{R_1} - \frac{1}{R_2} - \frac{1}{R_3} - \frac{1}{R_4} \right) \quad (6)$$

where Δn represents the difference between the ordinary refractive index $n_o$ of the lens 35_1, 35_2 and 35_3 and the extraordinary refractive index $n_e$ of the lens 35_1, 35_2 and 35_3; $R_1$ represents the curvature radius of front face 35_11 of the front lens 35_1; and $R_2$ represents the curvature radius of the interface surface 35_12 between the lens 35_1 and the sub-lens 37_1, $R_3$ represents the curvature radius of the interface surface 35_22 between the lens 35_2 and the sub-lens 37_2, and $R_4$ represents the curvature radius of the interface surface 35_32 between the lens 35_3 and the sub-lens 37_3.

As for the second embodiment each lens cell 39_1, 39_2 and 39_3 can be controlled independently by switching the rotator 33_1 or 33_2 and 33_2 of the corresponding lens cell. Consequently depending on the switching of the rotators 33_1 or 33_2 and 33_2 a set of different optical powers may be provided.

As way of example, again using $CaCO_3$ material for lens 35_1, 35_2 and 35_3 and with the following parameters:

| Δn | R1 | R2 | R3 | R4 |
|---|---|---|---|---|
| 0.17 | 200 mm | 283 mm | 485 mm | −425 mm |

An eight focal full field of view lens arrangement can be provided in which the focal can be switched between the following:

| C3 | C2 | C1 | P(Dpt) | Focal(m) |
|---|---|---|---|---|
| 0 | 0 | 0 | 0 | ∞ |
| 0 | 0 | 1 | 2 | 0.5 |
| 0 | 1 | 0 | 1.75 | 0.57 |
| 0 | 1 | 1 | 0.25 | 4 |
| 1 | 0 | 0 | 1.25 | 0.8 |
| 1 | 0 | 1 | 0.75 | 1.33 |
| 1 | 1 | 0 | 0.5 | 2 |
| 1 | 1 | 1 | 1.50 | 0.66 |

It will be appreciated that in further embodiments of the invention any number of lens cells may be used and configured to provide numerous combinations and to finely sample the viewing proximities provided. For J lens cells an optical power $P_T$ can be given as:

$$P_T = \Delta n \left( \frac{J}{R_1} - \frac{1}{R_2} - \ldots - \frac{1}{R_J} - \frac{1}{R_{J+1}} \right) \quad (7)$$

where Δn represents the difference between the first refractive index corresponding to the first optical power of the lens and the second refractive index corresponding to the second optical power of the lens; $R_1$ represents the curvature radius of front face of the combined lens; and $R_{J+1}$ represents the curvature radius of the interface surface between the Jth lens and its corresponding sub-lens.

In further embodiments of the invention the surfaces of the lens may be complex surfaces instead of spherical surfaces. With reference for example to FIG. 1A,B in the case where the surface of lens 15 are complex, the optical effect created at the interface surface 152 between lens 15 and sub lens 17 will depend on the curvature of the complex surface 152.

Now referring again for example to FIG. 7B the ophthalmic lens arrangement made up of three lens cells 39_1, 39_2 and 39_3 may be used to demonstrate different optical functions depending on the complex surfaces 35_12, 35_22 and 35_33 of the lens 35_1, 35_2 and 35_3. Such an arrangement may thus be used to provide an ophthalmic lens demonstration apparatus demonstrating a plurality of optical functions to a potential wearer of ophthalmic lens.

For example three individual optical functions may be each individually demonstrated in a sequential. To this end the rotators 33_1, 33_2 and 33_3 may be configured to be sequentially activated.

If rotator 33_1 is activated (rotators 33_2 and 33_3 remain inactive) the polarization of the light is rotated so that it encounters extraordinary refractive index $n_e$ in lens 35_1 while encountering ordinary refractive index $n_o$ in lenses 35_2 and 35_3. As described above in this embodiment of the invention sub lenses 37_1, 37_2 and 37_3 each have a refractive index of $n_o$. The optical function demonstrated will depend on the curvature of the interface surface 35_12 between lens 35_1 and lens element 37_1. The optical power of the combined lens arrangement will be $$P_1 = \Delta n \left( \frac{1}{R_1} - \frac{1}{R_2} \right) \quad (8)$$

Where R1 is the radius of the front surface 35_11 of lens 15 (and the front surface of the combined lens arrangement) and R2 is the radius of interface surface 35_12 between lens 35_1 and sub lens 37_1.

If rotator 33_2 is then activated (rotators 33_1 and 33_3 are inactive) the polarization of light is rotated by rotator 33_2 so that it encounters extraordinary refractive index $n_e$ in lens 35_2 while encountering ordinary refractive index $n_o$ in lenses 351 and 35_3. As described above sub lenses 37_1, 37_2 and 37_3 each have a refractive index of $n_o$. The optical function demonstrated will depend on the curvature of the interface surface 35_21 between lens 35_2 and lens element 37_2. The optical power of the combined lens arrangement will be $$P_1 = \Delta n \left( \frac{1}{R_1} - \frac{1}{R_3} \right) \quad (9)$$

Where R1 is the radius of the front surface 35_11 of lens 15 (and the front surface of the combined lens arrangement) and R3 is the radius of interface surface 35_22 between lens 35_2 and sub lens 37_2.

If rotator 33_3 is then activated (rotators 33_1 and 33_2 are inactive) the polarization of light is rotated by rotator 33_3 so that it encounters extraordinary refractive index $n_e$ in lens 35_3 while encountering ordinary refractive index $n_o$ in lenses 35_1 and 35_2. As described above sub lenses 37_1, 37_2 and 37_3 each have a refractive index of $n_o$. The optical function demonstrated will depend on the curvature of the interface surface 35_32 between lens 35_3 and lens element 37_3. The optical power of the combined lens arrangement will be $$P_1 = \Delta n \left( \frac{1}{R_1} - \frac{1}{R_4} \right) \quad (10)$$

Where R1 is the radius of the front surface 35_11 of lens 15 (and the front surface of the combined lens arrangement) and R4 is the radius of interface surface 35_32 between lens 35_3 and sub lens 37_3.

Moreover, two of the three rotators 33_1, 33_2 and 33_3 may be activated, or all three rotators 33_1, 33_2 and 33_3 may be activated to provide an optical power of:

$$P_T == \Delta n \left( \frac{3}{R_1} - \frac{1}{R_2} - \frac{1}{R_3} - \frac{1}{R_4} \right) \quad (11)$$

or alternatively none of the rotators 33_1, 33_2 and 33_3 may be activated to give an overall zero optical power.

Figure 8:
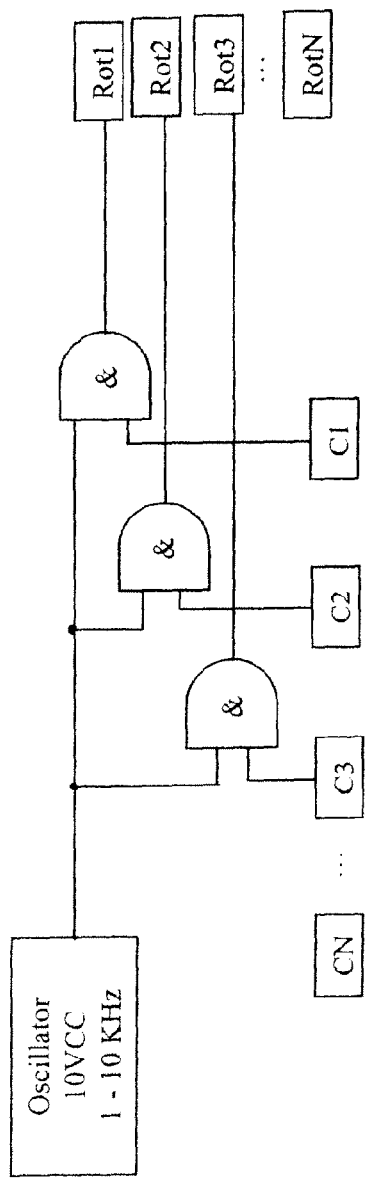
FIG. 8 is a schematic block diagram of an example of a control electronic for controlling the rotators of embodiments of the invention.

In the embodiments of the invention an electronic control can be used to control the rotators. An example of an electronic circuit providing logic control signals to N rotators C1 to CN is illustrated in FIG. 8. Signals based on specific optical functions to be demonstrated or on the proximity of the objects to be viewed through the ophthalmic lens arrangement may be fed to the control circuit so that the rotators may be controlled accordingly to provide the correct configurations for the required focalisation.

The ophthalmic demonstrator arrangement may be used in an optical demonstration facility such as an optician's lab to demonstrate to a patient or customer the different optical functions provided by different types of ophthalmic lenses thereby allowing the patient to compare them without individually trying different spectacles or lenses. This enables a potential wearer to test a range of optical functions on his or her viewing ability and to make an informed selection in the choice of optical lens for his or her spectacles. Moreover a uni-focal full field of vision will be demonstrated for each optical function.

The optical complex surfaces providing the optical functions may be progressive surfaces or for astigmatism. The surface may be sphero-toric, for example. To this end a particular lens cell of the ophthalmic lens arrangement may be dedicated to a progressive design, a particular optical power or an astigmatism. In this way one design may be compared to another.

An ophthalmic lens product for wearing providing different optical effects to correct astigmatism by using the differential between the two foci provided by the birefringent material used can be provided. One or both of the exterior lens surfaces of the combined lens cell configuration constituting the ophthalmic lens product can be machined accordingly to conform to the lens prescription of the wearer An ophthalmic arrangement of two lens cells may be used to form an ophthalmic lens product for wearing and may be configured to switch between two optical functions—for example a near vision function and a far vision function. Switching between the optical functions may be carried out manually or automatically. Automatically switching the rotators to switch between a far vision optical function and a near vision optical function may be carried out according to the proximity of the object being viewed through the ophthalmic lens arrangement. For example a detector of eye movement such as described in FR0953127 or FR0953126 in the name of Essilor may be used to determine if a far vision function or a near vision function is required. In this way the wearer of the optical product is provided with a full field of view for both near vision and for far vision, instead of having to look through a dedicated area of a lens surface for each optical function.

In the sense of the invention, "progressive surface" shall be understood as an optical surface, which is not rotationally symmetrical, with a continuous change of curvature over at least a part of the surface.

In the sense of the invention, "near vision zone" shall be understood as the zone of an optical function having the dioptric power for near vision.

In the sense of the invention, "far vision zone" shall be understood as the zone of an optical function having the dioptric power for far vision.

Figure 13:
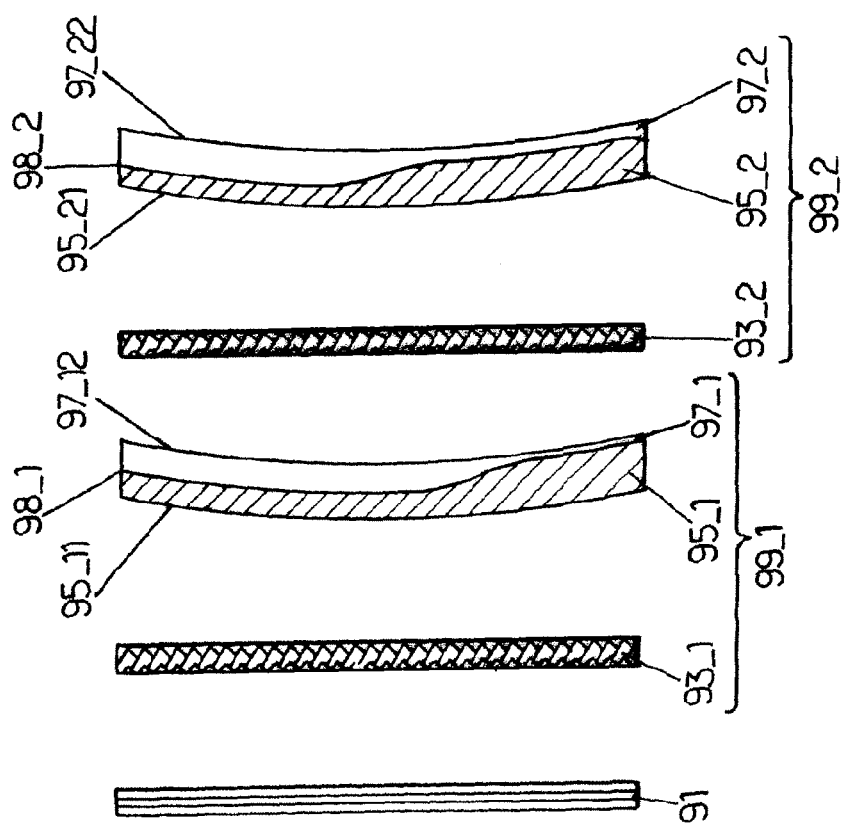
FIG. 13 shows an ophthalmic lens arrangement according to another embodiment of the invention.

For example with reference to FIG. 13 an ophthalmic lens arrangement according to another embodiment of the invention includes a polariser 91, a first lens cell 99_1 made up of a first rotator 93_1, a first lens 95_1 and a first sub-lens 97_1, and a second lens cell 99_2 made up of a second rotator 93_2, a second lens 95_2 and a second sub-lens 97_2.

The first and second lenses 95_1 and 95_2 have birefringence properties such that light passing through the lens medium follows different optical paths through the lens medium depending on its polarization. The light thus according to its direction of polarization either encounters an ordinary refractive index $n_o$ on an ordinary axis or an extraordinary refractive index $n_e$ on an extraordinary axis. To this end the lenses 95_1 and 95_2 are made of $CaCO_3$ material. It will be understood that in alternative embodiments, the lenses made be made of any suitable birefringent polymer material.

The first and second sub-lenses 97_1 and 97_2 have a refractive index $n_o$. The curvature of the external faces of the ophthalmic combination first lens 95_1 and first sub-lens 97_1 are matched i.e. the curvature of surface 95_11 of lens 95_1 and surface 97_12 of sub lens 97_1 are matched.

The curvature of the external faces of the ophthalmic combination second lens 95_2 and second sub-lens 97_2 are matched i.e. the curvature of surface 95_21 of lens 95_2 and surface 97_22 of sub lens 97_2 are matched.

The first lens cell 99_1 is arranged such that the intermediary surface 98_1 between the first lens 95_1 member and the first sub-lens member 97_1 is a progressive surface having a first optical function Prg1, for the light encountering the extraordinary index $n_e$. For example, said first optical function Prg1 comprises a near vision zone and a progressive corridor.

The second lens cell 99_2 is arranged such that the intermediary surface 98_2 between the second lens 95_2 member and the second sub-lens member 97_2 is a progressive surface having a second optical function Prg2, for the light encountering the extraordinary index $n_e$. For example, said second optical function Prg2 comprises a far vision zone and a progressive corridor.

In operation when the first rotator 93_1 is in the resting state the light encounters the ordinary refractive index $n_o$ of the first lens 95_1 and the refractive index $n_o$ of first sub lens 97_1. A combined lens of uniform refractive index $n_o$ with parallel matched faces and thus of zero power is provided.

However, on activation of the first rotator 93_1 the extraordinary refractive index $n_e$ of first lens 95_1 is selected. In this situation the light encounters the extraordinary refractive index $n_e$ in the first lens 95_1 and is refracted at the interface of the first lens 95_1 and the first sub lens 97_1. In this case an optical effect relative to the curvature of the interface and related to the differential $n_e-n_o$ is created. The optical function Prg1 is thus provided.

In operation, when the light encounters the ordinary refractive index $n_o$ of the second lens 95_2 and the refractive index $n_o$ of second sub lens 97_2. A combined lens of uniform refractive index $n_o$ with parallel matched faces and thus of zero power is provided. When the light encounters the extraordinary refractive index $n_e$ in the second lens 95_2, it is refracted at the interface of the second lens 95_2 and the second sub lens 97_2. In this case an optical effect relative to the curvature of the interface and related to the differential $n_e-n_o$ is created. The optical function Prg2 is thus provided.

Each lens cell 99_1 or 99_2 can be controlled independently by switching the rotator 93_1 or 93_2 of the corresponding lens cell. Consequently depending on the switching of the rotators 93_1 and 93_2 a set of different optical functions may be provided. According to an embodiment of the invention, the rotator 93_1 or 93_2 can not be switched on simultaneously.

In the case where the first rotator 93_1 is activated such that polarised light encounters the extraordinary refractive index $n_e$ of the first lens 95_1, while the second rotator 93_2 is inactive such that polarised light encounters the ordinary refractive index $n_o$ of the second lens 95_2, the optical function of the ophthalmic lens arrangement is the first optical function Prg1.

In the case where the first rotator 93_1 is inactive such that polarised light encounters the ordinary refractive index $n_o$ of the first lens 95_1, while the second rotator 93_2 is activated such that polarised light encounters the extraordinary refractive index $n_e$ of the lens 95_2, the optical function of the ophthalmic lens arrangement is the second optical function Prg2.

In the case where the two rotators 93_1 and 93_2 are inactive such that polarised light encounters the ordinary refractive index $n_0$ of both the lens 95_1 and the lens 95_2 the ophthalmic lens arrangement has a zero optical power.

A two function full field of view lens arrangement is provided in which the function can be switched between the following:

| C2 | C1 | Optical function |
|---|---|---|
| 0 | 0 | No function |
| 0 | 1 | Prg1 |
| 1 | 0 | Prg2 |

Where C1 and C2 correspond to the inactive (0) or activated state (1) of the rotators 93_1 and 93_2 respectively.

Advantageously, an optical product with a full field of view for both near vision and far vision can be provided to the wearer, instead of having to look through a dedicated area of a lens surface for each optical function. Furthermore, the optical artifacts, such as distortion, resulting astigmatism, and the spatial restrictions problems such as spatial distribution of the resulting astigmatism and the optical power over the surface of the progressive lens may be reduced.

Figure 14:
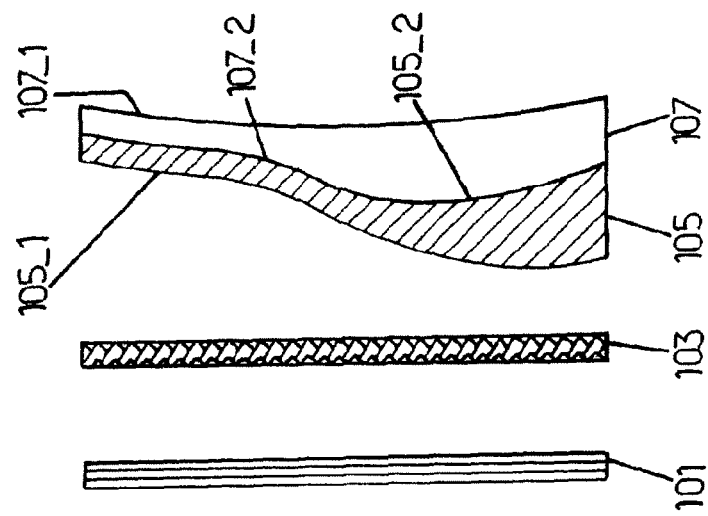
FIG. 14 an ophthalmic lens arrangement according to another embodiment of the invention.

With reference to FIG. 14 an ophthalmic lens arrangement according to another embodiment of the invention includes a polariser 101, a rotator 103, a lens 105 and a sub-lens 107.

The lens 105 have birefringence properties such that light passing through the lens medium follows different optical paths through the lens medium depending on its polarization. The light thus according to its direction of polarization either encounters an ordinary refractive index $n_o$ on an ordinary axis or an extraordinary refractive index $n_e$ on an extraordinary axis. To this end the lens 105 is made of $CaCO_3$ material. It will be understood that in alternative embodiments, the lens may be made of any suitable birefringent polymer material. The sub lens 107 has a refractive index $n_o$.

The ophthalmic combination comprise a lens 105 and sub-lens 107. The lens 105 comprises two faces 105_1 and 105_2, which are complex surfaces. The sub-lens 107 comprises an external face 107_1 and a internal face 107_2, said internal face 107_2 matches the face 105_2 of the lens 105. The external surfaces 105_1 and 107_1 of the said ophthalmic combination are arranged such that a first optical function is provided for the light encountering the ordinary index $n_o$. For example, the first optical function provided is a progressive optical function Prg1. For example, said first progressive optical function Prg1 comprises a near vision zone and a progressive corridor.

The ophthalmic combination, lens 105 and sub-lens 107, is arranged such that the intermediary surface 105_2 between the lens 105 and the sub-lens 107 is a complex surface providing a second optical function for the light encountering the extraordinary index $n_e$ of the lens 105. For example, the second optical function is a progressive optical function Prg2. For example, said second progressive optical function Prg2 comprises a far vision zone and a progressive corridor.

In operation when the rotator 103 is in the resting state the light encounters the ordinary refractive index $n_o$ of the lens 105 and the refractive index $n_o$ of the sub lens 107. In this case, the optical effect relative to the curvature of the external faces 105_1 and 107_2 of the ophthalmic combination and the reflective index $n_o$ is provided. The first progressive optical function Prg1 is thus provided.

However, on activation of the rotator 103 the extraordinary refractive index $n_e$ of lens 105 is selected. In this situation the light encounters the extraordinary refractive index $n_e$ in the lens 105 and is refracted at the interface 105_2 of the lens 105 and the sub lens 107. In this case an optical effect relative to the curvature of the interface, related to the differential $n_e - n_o$, and related to the curvature of the external faces of the ophthalmic combination is created. The second progressive optical function Prg2 is thus provided.

The invention is not limited to the specific progressive optical functions Prg1 and Prg2. For example, according to an embodiment of the invention, the progressive optical function Prg1 could comprises a far vision zone and a progressive corridor. Said progressive optical functions may be adapted to a specific activity of the wearer, such as driving, computing activity, sports etc. . . .

The ophthalmic combination, lens 105 and sub lens 107, can be controlled by switching the rotator 103. Consequently depending on the switching of the rotator 103 different optical functions may be provided.

In the case where the rotator 103 is activated such that polarised light encounters the extraordinary refractive index $n_e$ of the lens 105, the optical function of the ophthalmic lens arrangement is the second progressive optical function Prg2.

In the case where the rotator 103 is inactive such that polarised light encounters the ordinary refractive index $n_o$ of the lens 105, the optical function of the ophthalmic lens arrangement is the first progressive optical function Prg1.

A two function full field of view lens arrangement is provided in which the function can be switched between the following:

| C1 | Optical function |
|---|---|
| 1 | Prg2 |
| 0 | Prg1 |

Where C1 corresponds to the inactive (0) or activated state (1) of the rotator 103.

Advantageously, an optical product with a full field of view for two different optical functions is provided to the wearer by using a single ophthalmic combination lens 105 and sub lens 107.

In other embodiments the sub lens may have a refractive index n which is not equal to $n_o$ or $n_e$.

Figure 9:
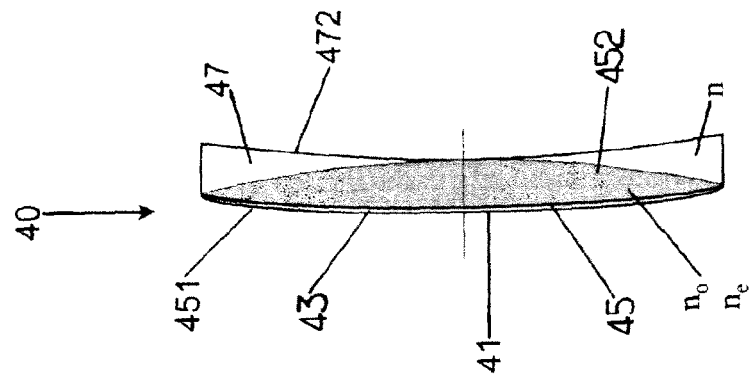
FIG. 9 is a schematic diagram of an ophthalmic lens arrangement according to the fourth embodiment of the invention.

With reference to FIG. 9 ophthalmic lens arrangement 40 including polariser 41, rotator 43, lens 45 and sub lens 57. Lens 45 has birefringent properties and is similar to lens 15 of the first embodiment having refractive indexes $n_o$ and $n_e$ depending on the polarisation of the light. Sub lens 47 has a refractive index n different to $n_o$ or $n_e$. The radius of the curvature of the front face 451 of lens 45 and the back face 472 of sub lens 47 are matched. In this case the refractive index n is different to $n_o$ or $n_e$, the refractive indexes of lens 45. When the rotator 43 is inactive such that light encounters ordinary refractive index $n_o$ an optical power $P_o$ is provided as set out below. Otherwise when the rotator 43 is activated to rotate the polarisation of light by 90°, an optical power $P_e$ is provided as set out below $$\boxed{\begin{aligned} P_o &= (n_o - n)\left(\frac{1}{R_1} - \frac{1}{R_2}\right) \\ P_e &= (n_e - n)\left(\frac{1}{R_1} - \frac{1}{R_2}\right) \end{aligned}} \quad (12)$$

where $R_1$ is the radius of the curvature of the front face 451 of lens 45 and $R_2$ represents the radius of the curvature of the interface face 452 between lens 45 and sub lens 47.

The range of power ΔP provided by the optical lens arrangement 40 can there by be moved with the optical power range. For example:

if $n_o = n = 1.3$, $n_e = 1.47$, $R_1 = 0.3$ m, $R_2 = -0.2$ m, optical powers $P_o = 0\delta$ and $P_e = 1.41\delta$ are obtained if $n_o = 1.3$, $n_e = 1.47$, $n = 1.2$, $R_1 = 0.3$ m, $R_2 = -0.2$ m optical powers $P_o = 0.838\delta$ and $P_e = 2.24\delta$ are obtained.

Thus the range width of power ΔP provided by the optical lens arrangement remains unchanged but can be moved within the full optical power range.

In the case where the radius of the curvature front face 451 of lens 45 and the back face 472 of sub lens 47 are not matched an extra degree of liberty in defining the optical power provided is introduced.

When the rotator 43 is inactive such that light encounters ordinary refractive index $n_o$ an optical power $P_o$ is provided:

$$P_o = \frac{n_o - 1}{R_1} + \frac{n - n_o}{R_2} + \frac{1 - n}{R_3} \quad (13)$$

Otherwise when the rotator 43 is activated to rotate the polarisation of light by 90°, an optical power $P_e$ is provided:

$$P_e = \frac{n_e - 1}{R_1} + \frac{n - n_e}{R_2} + \frac{1 - n}{R_3} \quad (14)$$

where $R_1$ is the radius of the curvature of the front face 451 of lens 45, $R_2$ represents the radius of the curvature of the interface face 452 between lens 45 and sub lens 47 and $R_3$ is the radius of the curvature of the back face 472 of sub lens 47.

As in the previous example the optical power range ΔP provided by the combined lens arrangement remains the same but can be moved within the optical power range by adjusting n and/or the radius R3. It will be appreciated that the curvature radii $R_1$ and $R_2$ may also be changed, for example by increasing in them with the aim of reducing the overall thickness of the optical lens arrangement 40.

It is thus possible in the previous two examples to provide a non-zero dioptre power to the ophthalmic lens arrangement in its non-activated state. This dioptre power can correspond to the refraction of the wearer of the ophthalmic lens product.

Toric shaped surfaces may be provided on the lens and the sub lens. In this case the toric surface will have two radii Rt, Rs as well as an axis. A far vision refraction may thus be provided and different optical powers (additions) may be added to enable access to different viewing proximities. The astigmatism value for each proximity can be distinguished in order to optimise the refraction provided to the wearer.

Figure 11:
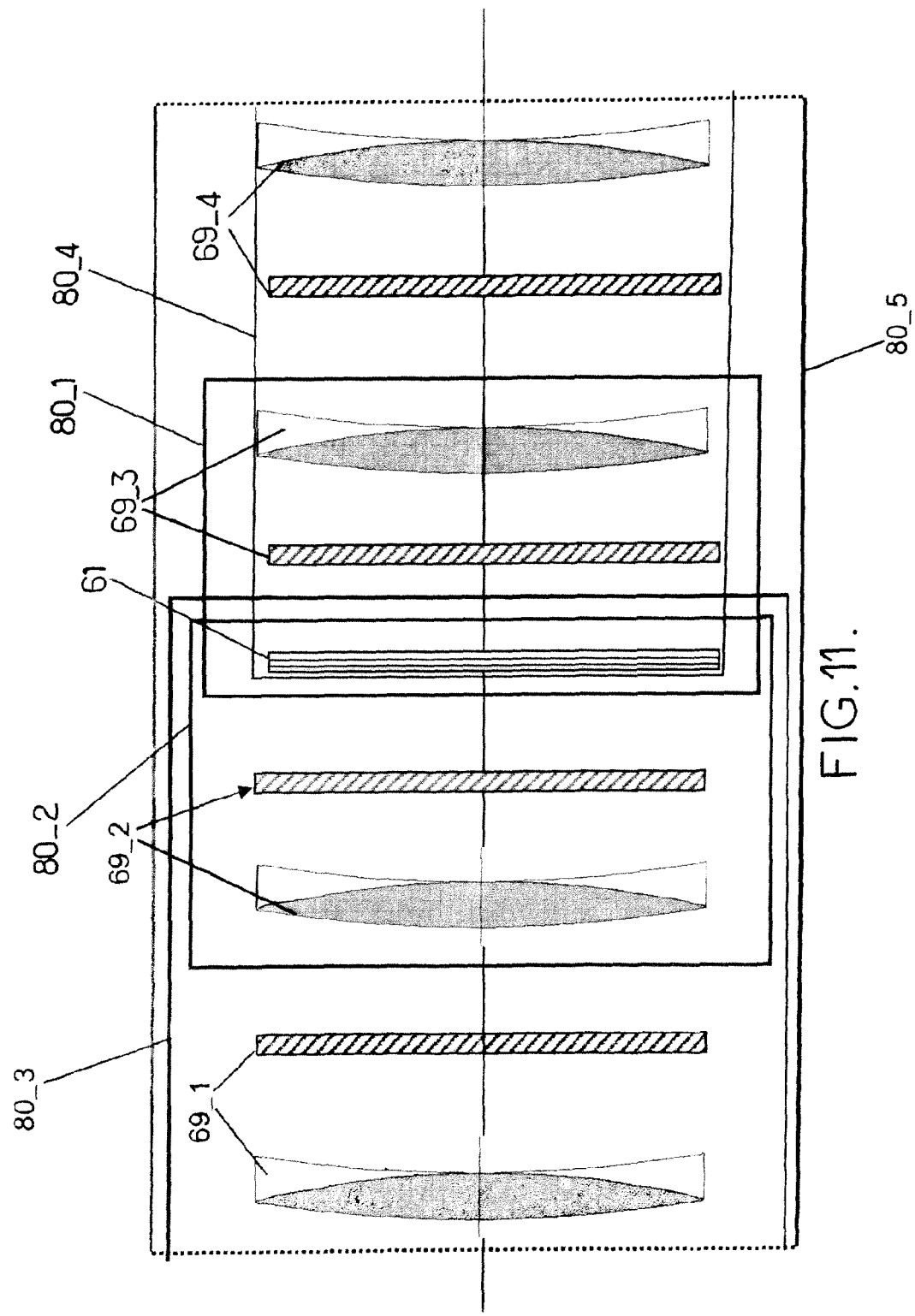
FIG. 11 is a schematic diagram of an ophthalmic lens arrangement according to the sixth embodiment of the invention.

Moreover while the foregoing embodiments have been described with reference to an ophthalmic lens arrangement in which a polariser is positioned before the rotator and the lens and sub lens combination, it will be appreciated that in further embodiments of the invention the polariser 51 may be positioned after the rotator 53, the rotator 53 being positioned after the lens 55 and sub lens 57 combination as illustrated in a fifth embodiment of the invention illustrated in FIG. 10A or 10B. Moreover combination of different lens cells 69_1 to 69_4 with the polariser 61 positioned at different positions with respect to the lens cells 69_1 to 69_4 may be provided individually or in different combinations (80_1 to 80_5) as illustrated in FIG. 11 according to various embodiments of the invention.

Although the present invention has been described hereinabove with reference to specific embodiments, the present invention is not limited to the specific embodiments, and modifications will be apparent to a skilled person in the art which lie within the scope of the present invention.

For instance, while the foregoing examples have been explained with respect to a lens made of birefringent material CaCO3 it will be appreciated that any other suitable birefringent material may be used, for example as cited in the document "Highly birefringent materials designed using coordination polymer synthetic methodology by KATZ et al. Differentials Δn in the ordinary refractive index $n_o$ and the extraordinary refractive index $n_e$ of the order of 0.4 may be obtained. The radii of the curvatures of the lens may be reduced using such a differential leading to a reduction in the thickness of the lens cell and thus reducing the ophthalmic lens arrangement to a size approaching the size of a conventional ophthalmic lens arrangement.

Figure 12B:
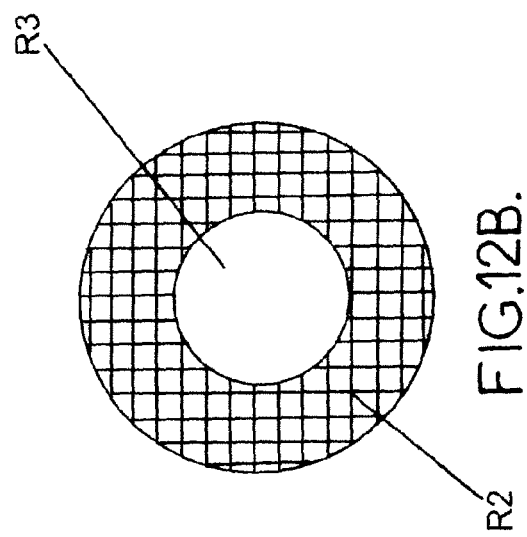
FIGS. 12A and 12B are schematic diagram of alternative embodiments of a rotator for ophthalmic lens arrangements according to embodiments of the invention.
Figure 12A:
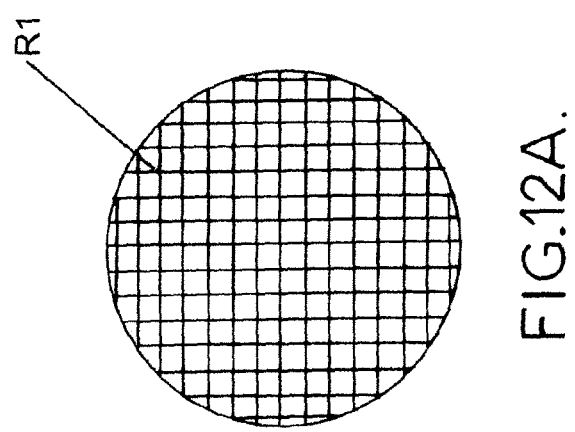

In some embodiments of the invention a rotator R1 having a cellular structure such as is illustrated in FIG. 12A may be used to rotate the polarisation of the light. In such a structure the rotator is divided into a matrix of rotator cells so that when the edges of the lens arrangement are cut in accordance with lens manufacturing methods the entire rotator is not damaged but instead only a number of rotator cells are removed leaving the inner rotator cells to function as normal. Alternatively as illustrated in FIG. 12B only the peripheral area liable to be cut may be provided in cellular form R2 while the central area R3 of an zone unlikely to be cut during manufacture is made up of a non cellular type rotator.

Many further modifications and variations will suggest themselves to those versed in the art upon making reference to the foregoing illustrative embodiments, which are given by way of example only and which are not intended to limit the scope of the invention, that being determined solely by the appended claims. In particular the different features from different embodiments may be interchanged, where appropriate.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. An ophthalmic lens arrangement comprising:
 a polariser for polarising light in a polarisation axis; and
 a lens cell including:
    a switchable light rotator operable to rotate incident light by 0° or by 90°;
    a lens member having birefringence properties such that incident light encounters a first refractive index $n_o$ on an ordinary axis or a second refractive index $n_e$ on an extraordinary axis according to the rotation of the incident light; and
    a sub lens member having a refractive index, wherein:
       the polariser is arranged such that the polarisation axis coincides with either the ordinary axis or the extraordinary axis of the lens member, and
       the lens member includes an intermediary surface immediately adjacent to the sub-lens member of the lens cell, the intermediary surface being a progressive surface.

2. An ophthalmic lens arrangement according to claim 1 wherein the refractive index of the sub lens member is $n_o$ or $n_e$.

3. An ophthalmic lens arrangement according to claim 2, wherein the lens cell has external faces that are matched such that an optical power of the lens cell is zero along the ordinary axis or along the extraordinary axis.

4. An ophthalmic lens arrangement according to claim 1 wherein the rotator is adjusted to rotate the incident light to provide an optical power of the ophthalmic lens arrangement within a predetermined optical power range that depends on the refractive index of each of the at least one sub lens member.

5. An ophthalmic lens arrangement according to claim 1 wherein an external face of the ophthalmic lens arrangement is machinable to conform to an ophthalmic lens prescription.

6. An ophthalmic lens arrangement according to claim 1 wherein the intermediary surface is a sphero-toric surface.

7. An ophthalmic lens arrangement according to claim 1 wherein the rotator is switchable from a first state to a second state providing a change in dioptric values of the ophthalmic lens arrangement.

8. An ophthalmic lens arrangement according to claim 1 wherein the rotator is configured to be switched according to the proximity of an object being viewed through the ophthalmic lens arrangement.

9. An apparatus for demonstrating a plurality of optical functions, the apparatus comprising:
 an ophthalmic lens arrangement including:
 a polariser for polarising light in a polarisation axis; and
 a plurality of lens cells, each lens cell including:
    a switchable light rotator operable to rotate incident light by 0° or by 90°;
    a lens member having birefringence properties such that incident light encounters a first refractive index $n_o$ on an ordinary axis or a second refractive index $n_e$ on an extraordinary axis according to the rotation of the incident light; and
    a sub lens member having a refractive index, wherein:
       the polariser is arranged such that the polarisation axis coincides with either the ordinary axis or the extraordinary axis of the lens member, and
       the lens member includes an intermediary surface immediately adjacent to the sub-lens member of the lens cell, the intermediary surface being a progressive, complex surface; and a selector for switching the rotator of one or more of the lens cells according to the optical functions to be demonstrated;

wherein the optical functions to be demonstrated include at least progressive design and astigmatism design.

10. An apparatus according to claim 9 wherein:

the refractive index of at least one of the sub lens members is $n_o$ or $n_e$ and external faces of the corresponding lens cells are matched such that an optical power of each lens cell is zero along the ordinary axis or along the extraordinary axis; and the selector is arranged to select the optical functions to be demonstrated by switching the rotator of at least one of the lens cells such that the optical power of the lens cell is zero along the ordinary axis or along the extraordinary axis is zero, and by switching the rotator of another lens cell of the plurality so that the another lens cell has a non-zero optical power.

11. An apparatus according to claim 9 wherein the selector is operable to switch the rotator of each lens cell such that a single lens cell of the lens cells is sequentially selected to have a non-zero optical power while the remaining lens cells have a zero optical power.

12. An apparatus according to claim 9 wherein at least one of the rotators is adjusted to rotate the incident light to provide an optical power of the ophthalmic lens arrangement within a predetermined optical power range that depends on the refractive index of each of the sub lens members.

13. An apparatus according to claim 9 wherein an external face of the ophthalmic lens arrangement is machinable to conform to an ophthalmic lens prescription.

14. An apparatus according to claim 9 wherein the lens member of at least one of the lens cells includes a sphero-toric surface immediately adjacent to the corresponding sub-lens member.

15. An apparatus according to claim 9 wherein at least one of the rotators is switchable from a first state to a second state providing a change in dioptric values of the ophthalmic lens arrangement.

16. An apparatus according to claim 9 wherein each of the rotators is configured to be switched according to the proximity of an object being viewed through the ophthalmic lens arrangement.

17. A method of demonstrating a plurality of optical functions of an ophthalmic lens, the method comprising:

selecting an optical function to be demonstrated;

polarizing light;

transmitting light through a plurality of lens cells wherein each lens cell includes:

a lens member having birefringence properties such that incident light encounters a first refractive index $n_o$ or a second refractive index $n_e$ according to the rotation of the incident light; and a sub lens member having a refractive index;

rotating the light entering each lens member from a first incident direction by 0° or by 90° according to which of the optical functions is to be demonstrated.

18. A method according to claim 17 comprising switching the rotator of each lens cell such that a single lens cell of the lens cells is sequentially selected to have a non-zero optical power while the remaining lens cells have a zero optical power.

* * * * *